United States Patent [19]

Bluthé et al.

[11] Patent Number: 4,556,742
[45] Date of Patent: Dec. 3, 1985

[54] PROCESS FOR THE PREPARATION OF α,δ-DIETHYLENIC CARBONYL COMPOUNDS

[75] Inventors: Norbert Bluthé, Villeurbanne; Armand S. Falou, Choiseul; Jacques Goré, Caluire, all of France

[73] Assignee: Rhone-Poulenc Sante, Courbevoie, France

[21] Appl. No.: 614,218

[22] Filed: May 25, 1984

[30] Foreign Application Priority Data

May 27, 1983 [FR] France ................ 83 08809

[51] Int. Cl.$^4$ .............................................. C07C 45/51
[52] U.S. Cl. ...................................... 568/403; 568/361
[58] Field of Search ............................... 568/403, 361

[56] References Cited

U.S. PATENT DOCUMENTS

4,453,011  6/1984  Schulte-Elte et al. ............ 568/403

FOREIGN PATENT DOCUMENTS

64579 10/1949 Netherlands ................... 568/403

OTHER PUBLICATIONS

Rhoads et al., "Organic Reactions", vol. 22, pp. 61–65.

*Primary Examiner*—James H. Reamer
*Attorney, Agent, or Firm*—Stevens, Davis, Miller & Mosher

[57] ABSTRACT

α,δ-Diethylenic carbonyl compounds of the formula

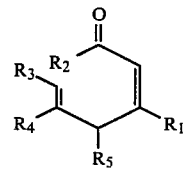

(I)

are made by an oxy-Cope rearrangement of an acetylenic alcohol of the formula

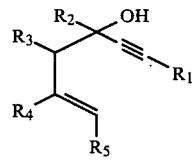

(II)

in the presence of a catalyst based on a metal of Group Ib of the periodic table or palladium. In the formulae (I) and (II), $R_1$, $R_2$, $R_3$ and $R_4$, which may be identical or different, each denote a hydrogen atom or a hydrocarbon radical $R_2$ and $R_3$ being capable together of forming an alkylene radical $(-CH_2-)_n$ in which one or more carbon atoms may be substituted by one or more alkyl radicals containing 1 to 4 carbon atoms, n is 3 to 20 inclusively and $R_5$ denotes a hydrogen atom.

9 Claims, No Drawings

PROCESS FOR THE PREPARATION OF α,δ-DIETHYLENIC CARBONYL COMPOUNDS

The present invention provides a process for the preparation of α,δ-diethylenic carbonyl compounds of the formula:

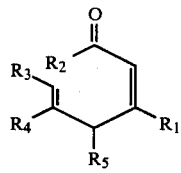
(I)

in which $R_1$, $R_2$, $R_3$ and $R_4$, which may be identical or different, each denote a hydrogen atom or a hydrocarbon radical, it being understood that $R_2$ and $R_3$ can together form an alkylene radical $(-CH_2-)_n$ in which one or more carbon atoms are unsubstituted or substituted by one or more alkyl radicals containing 1 to 4 carbon atoms each and n is an integer from 3 to 30, $R_5$ denotes a hydrogen atom, and $R_2$ and $R_5$ can together form a ring containing from 6 to 16 chain members, by rearrangement of an acetylenic alcohol of the formula:

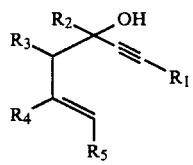
(II)

in which $R_1$, $R_2$, $R_3$, $R_4$ and $R_5$ are defined as above in the presence of a novel catalyst as described below.

The aforesaid hydrocarbon radicals may be acyclic radicals of 1 to 20 carbon atoms each, the chain of which may contain one or more double or triple bonds.

The compounds of the formula (I) in which $R_1$ and $R_5$ denote a hydrogen atom, $R_2$ and $R_4$ denote a methyl radical and $R_3$ denotes a hydrogen atom or a 3-methyl-2-butenyl radical or 3,7-dimethyl-2,6-octadienyl radical are of particular interest.

The compounds of formula (I) are particularly valuable intermediates in organic synthesis. More particularly, the process of the present invention provides access to pseudo-ionone and its isomers which are used to prepare Vitamins A and E, β-carotene or squalane, to farnesylacetone which makes it possible to prepare Vitamin E through the intermediary of phytone, or to the cyclanones which lead to products which can be employed in perfumery.

Rearrangement of acetylenic alcohols to unsaturated ketones is a type of reaction called an oxy-Cope rearrangement. The oxy-Cope rearrangement has been the subject of many investigations but, on account of conditions employed for its application, its practical value has been very limited. More particularly, the thermal rearrangement of acetylenic alcohols to provide access to compounds of the terpene type has been studied by T. Onishi and coworkers, Synthesis, 651–654 (1980). The major disadvantage of the thermal rearrangement lies in the instability of the allenic enol which is the primary product of the reaction, and in the occurrence of unwanted secondary reactions (ene and retro-ene reactions). The thermal rearrangement can be improved by operating in the presence of suitable solvents such as N-methylpyrrolidone, hexamethylphosphotriamide or dimethyl sulphoxide, but the selectivity is unsatisfactory.

The thermal rearrangement of propargyl alcohols has been employed for the preparation of ionones or irones (French Pat. No. 78/15,136 published under No. 2,391,893) and unsaturated ketones (French Pat. No. 77/03,951 published under No. 2,340,923).

It has now been found, and this is the subject of the present invention, that the oxy-Cope rearrangement of the acetylenic alcohols of the general formula (II) can be carried out selectively by operating at a temperature below 100° C. in the presence of a suitable catalyst.

The catalysts which are suitable for use in the process of the present invention are based on the metals of Group Ib of the periodic table and palladium. More particularly, the metals whose derivatives are especially suitable are copper, silver and gold. Among these derivatives may be mentioned cuprous chloride, cuprous bromide, cupric chloride, cuprous acetate, silver trifluoromethanesulphonate, silver nitrate, silver borofluoride, silver acetate, gold chloride and cyclooctadienylpalladium chloride [$PdCl_2$(cyclooctadienyl)].

In general, the catalyst is employed at a concentration of 0.001 to 1 mole per mole of acetylenic alcohol.

To improve catalyst reactivity and the selectivity of the reaction by eliminating the secondary polymerisation reactions, it is advantageous to operate in the presence of a salt of an alkali metal or a quaternary ammonium salt. Among the salts which are particularly suitable may be mentioned sodium, potassium, lithium or caesium halides (chlorides, fluorides), nitrates and trifluoroacetates, or tetrabutylammonium chloride.

If appropriate, the oxy-Cope rearrangement may be carried out in the presence of a solvent or a mixture of solvents such as a ketone (eg. acetone), an alcohol (eg. ethanol), an ether (eg. isopropyl ether), a chlorinated solvent (eg. chlorobenzene), a nitrile (eg. acetonitrile), an aliphatic hydrocarbon (eg. hexane) or a mixture of tetrahydrofuran with water or methylene chloride with dimethylformamide.

In general, the reaction time is between 15 minutes and 50 hours, the temperature being between 0° and 100° C.

The diethylenic ketone of the general formula (I) is generally isolated by the usual methods and, if appropriate, after treatment of the reaction mixture with a basic aqueous solution such as a saturated solution of sodium bicarbonate. It may be purified by the use of physical methods such as distillation.

The process according to the present invention makes it possible to obtain α,δ-diethylenic ketones in good yields, which can vary, however, depending on the nature of the acetylenic alcohol employed. Moreover, the process is stereoselective and generally produces a major proportion of one of the isomers.

Furthermore, it is possible to employ α,δ-diethylenic ketones obtained according to the process of the present invention without preliminary isolation and purification. For example, the raw reaction product may be catalytically hydrogenated to the corresponding saturated ketone, with yields which are generally greater than 80% based on the acetylenic alcohol employed.

The following examples illustrate the invention.

EXAMPLE 1

4-Isopropenyl-3,7-dimethyl-6-octen-1-yn-3-ol (0.192 g; $10^{-3}$ mole) is kept at a temperature in the region of 40° C. and protected from light in the presence of silver trifluoromethanesulphonate (0.257 g; $10^{-3}$ mole) in a mixture (3:1 by volume) of tetrahydrofuran and water (10 cc). After 20 hours the reaction mixture is diluted with ethyl ether (20 cc) and treated with a saturated solution of sodium bicarbonate (5 cc). After separation, the organic phase is washed with demineralised water until neutral, and then dried over magnesium sulphate. After filtration, evaporation of the solvent under reduced pressure (20 mm Hg; 2.7 kPa) and purification by chromatography on alumina, 6,10-dimethyl-3,6,8-undecatrien-2-one (0.110 g) is obtained in a yield of 57%, having the following characteristics:

Infrared spectrum (liquid film): characteristic bands at 3,080, 3,030, 1,670, 1,625, 1,360, 1,250 and 980 cm$^{-1}$.

NMR spectrum (CDCl$_3$; δ in ppm, J in Hz): 1.57 (s, 6H); 1.63 (s, 3H), 2.19 (s, 3H), 2.64 (t, 2H, J=7); 2.80 (d, 2H, J=7); 5.02 (pert. t, 1H, J=7); 5.12 (pert. t, 1H, J=7); 6.00 (d, 1H, J=15); 6.70 (d×t, 1H, J$_1$=15, J$_2$=7).

6,10-Dimethyl-3,6,8-undecatrien-2-one can be obtained by operating as in Example 1 but changing the nature of the catalyst and, if appropriate, the co-catalyst, the solvent, the temperature and the reaction time.

The results are collated in the following table:

| Examples | Catalyst | % (molar) relative to the alcohol | Co-catalyst | % (molar) relative to the alcohol | Solvent | Temperature (°C.) | Time (hours) | Degree of conversion | Yield (based on the converted product) |
|---|---|---|---|---|---|---|---|---|---|
| 2 | AgOSO$_2$CF$_3$ | 10 | — | — | acetone | 20 | 14 | 32 | 75 |
| 3 | AgNO$_3$ | 10 | — | — | acetone | 40 | 8 | 45 | 33 |
| 4 | AgBF$_4$ | 10 | — | — | THF—water (2:1 by vol.) | 66 | 40 | 55 | 43 |
| 5 | AgBF$_4$ | 23 | | | CH$_2$Cl$_2$—DMF (2:1 by vol.) | 50 | 4 | 95 | 67 |
| 6 | AgNO$_3$ | 10 | KNO$_3$ | 80 | THF—water (2:1 by vol.) | 66 | 24 | 98 | 40 |
| 7 | AgNO$_3$ | 10 | CsNO$_3$ | 80 | THF—water (2:1 by vol.) | 66 | 50 | 98 | 35 |
| 8 | AgNO$_3$ | 10 | KNO$_3$ | 20 | THF—water (2:1 by vol.) | 66 | 15 | 94 | 45 |
| 9 | AgNO$_3$ | 10 | KNO$_3$ | 23 | THF—water (2:1 by vol.) | 66 | 13 | 61 | 64 |
| 10 | AgNO$_3$ | 10 | KNO$_3$ | 300 | THF—water (2:1 by vol.) | 66 | 13 | 60 | 66 |
| 11 | AgNO$_3$ | 20 | KNO$_3$ | 100 | THF—water (2:1 by vol.) | 66 | 73 | 100 | 30 |
| 12 | AgNO$_3$ | 20 | KNO$_3$ | 100 | THF—water (2:1 by vol.) | 66 | 15 | 100 | 52 |
| 13 | AgOCOCF$_3$ | 9 | | | THF—water (1:1 by vol.) | 20 | 48 | 85 | 34 |
| 14 | AgOCOCF$_3$ | 21 | LiOCOCF$_3$ | 68 | THF—water (1:1 by vol.) | 40 | 7.5 | 95 | 65 |
| 15 | CuOCOH$_3$ | 20 | | | CH$_2$Cl$_2$—DMF (2:1 by vol.) | 50 | 4 | 63 | 75 |
| 16 | CuCl$_2$ | 21 | | | CH$_2$Cl$_2$—DMF (2:1 by vol.) | 50 | 4 | 35 | 55 |
| 17 | CuCl | 20 | | | CH$_2$Cl$_2$-DMF (2:1 by vol.) | 50 | 4 | 91 | 81 |
| 18 | CuBr | 20 | | | CH$_2$Cl$_2$—DMF (2:1 by vol.) | 50 | 4 | 18 | 58 |
| 19 | CuCl | 20 | | | isopropyl ether | 60 | 6 | 17 | 52 |
| 20 | CuCl | 20 | | | THF—water (1:1 by vol.) | 60 | 6 | 24 | 34 |
| 21 | CuCl | 20 | | | ethanol | 60 | 6 | 25 | 57 |
| 22 | CuCl | 20 | | | C$_6$H$_5$Cl | 60 | 6 | 32 | 79 |
| 23 | CuCl | 20 | | | hexane | 60 | 6 | 55 | 71 |
| 24 | CuCl | 20 | | | acetonitrile | 60 | 6 | 76 | 80 |
| 25 | CuCl | 20 | | | | 60 | 6 | 94 | 80 |
| 26 | CuCl | 20 | | | | 100 | 0.25 | 88 | 89 |
| 27 | CuCl | 20 | LiCl | 45 | | 100 | 0.25 | 99 | 91 |
| 28 | CuCl | 5.7 | LiCl | 6.1 | | 100 | 0.5 | 77 | 91 |
| 29 | CuCl | 4.8 | NaCl | 6.4 | | 100 | 0.5 | 89 | 81 |
| 30 | CuCl | 5.7 | KCl | 7 | | 100 | 0.5 | 95 | 87 |
| 31 | CuCl | 20 | (C$_4$H$_9$)$_4$N$^+$Cl$^-$ | 19 | | 60 | 13 | 69 | 78 |
| 32 | CuCl | 20 | LiOCOCF$_3$ | 24 | | 60 | 4 | 98 | 91 |
| 33 | CuCl | 20 | NaOCOCH$_3$ | 31 | | 56 | 4 | 76 | 83 |
| 34 | CuCl | 21 | NaF | 54 | | 60 | 2 | 83 | 92 |
| 35 | CuCl | 2 | KCl | 3.3 | | 100 | 2 | 94 | 90 |

EXAMPLE 36

A mixture of 3,7-dimethyl-4-isopropenyl-6-octen-1-yn-3-ol (0.5896 g; 3.07×$10^{-3}$ mole), cyclooctadienyl-palladium dichloride (0.082 g; 0.29×$10^{-3}$ mole) and lithium chloride (0.1492 g; 3.5×$10^{-3}$ mole) is kept stirred for 11 hours at a temperature of 60° C. The reaction mixture is then filtered through a column of silica and eluted with ethyl ether. After the eluant has been evaporated off, the product obtained is distilled at a temperature below or equal to 240° C. under reduced pressure (0.1 mm Hg; 0.013 kPa). A mixture (0.223 g) of 6,10-dimethyl-3,5,9-undecatrien-2-one (pseudoionone) and 6,10-dimethyl-3,6,9-undecatrien-2-one, containing less than 3% of unconverted alcohol, is thus obtained. The degree of conversion is 99% and the yield based on the converted product is 28%.

reaction time. The results are collated in the following table:

| Examples | Catalyst | % (molar) relative to the alcohol | Co-catalyst | % (molar) relative to the alcohol | Solvent | Temperature (°C.) | Time (hours) | Degree of conversion | Yield (based on the converted product) |
| --- | --- | --- | --- | --- | --- | --- | --- | --- | --- |
| 39 | AgOSO$_2$CF$_3$ | 100 | | | THF—water (3:1 by vol.) | 20 | 48 | 88 | 62 |
| 40 | AgNO$_3$ | 100 | | | THF—water (5:1 by vol.) | 20 | 16 | 89 | 58 |
| 41 | AgNO$_3$ | 10 | KNO$_3$ | 110 | THF—water (2:1 by vol.) | 66 | 13 | 66 | 70 |

Hydrogenation in the presence of palladium on charcoal (5% in ethanol) produces exclusively 6,10-dimethyl-undecan-2-one, the $^{13}$C NMR spectrum of which shows the following peaks (δ in ppm; tetramethylsilane in CDCl$_3$ as internal reference): 19.4; 21.4; 22.4; 22.5; 24.6; 27.9; 29.5; 32.6; 36.5; 37.1; 39.3; 44.0 and 208.3.

EXAMPLE 37

A mixture of 3,7-dimethyl-4-isopropenyl-6-octen-1-yn-3-ol (0.4928 g); 2.56×10$^{-3}$ mole), auric chloride (AuCl$_3$.2H$_2$O) (0.0883 g; 2.6×10$^{-4}$ mole) and potassium chloride (0.0211 g; 2.8×10$^{-4}$ mole) is kept stirred for 6 hours at a temperature of 60° C. The reaction mixture is then filtered through a column containing silica (2 g) and eluted with ethyl ether. After the eluant has been evaporated off under reduced pressure, a mixture (0.443 g) is obtained, consisting essentially of 6,10-dimethyl-3,5,9-undecatrien-2-one (pseudoionone), 6,10-dimethyl-3,6,9-undecatrien-2-one and approximately 1.5% of the starting alcohol.

The mixture obtained is hydrogenated in the presence of 10% by weight of palladium on charcoal (5% in ethanol). After filtration and evaporation of the solvent, only 6,10-dimethylundecan-2-one is obtained.

EXAMPLE 38

4-Isopropenyl-3,7,11-trimethyl-6,10-dodecadien-1-yn-3-ol (0.260 g; 10$^{-3}$ mole) is kept at the reflux temperature of tetrahydrofuran and protected from light, in the presence of silver nitrate (0.017 g; 10$^{-4}$ mole) and potassium nitrate (0.101 g; 10$^{-3}$ mole) in a mixture (6 cc) of tetrahydrofuran and water (2:1 by volume). After being heated under reflux for 15 hours, the reaction mixture is treated under the conditions described in Example 1. 6,10,14-Trimethyl-3,6,9,13-pentadecatraen-2-one (0.120 g) is thus obtained, with the following characteristics:

Infrared spectrum (liquid film): characteristic bands at 3,030, 1,680, 1,630, 1,255 and 985 cm$^{-1}$.

NMR spectrum (CDCl$_3$; δ in ppm; J in Hz): 1.55–1.72 (m, 12H), 1.88–2.12 (m, 4H), 2.15 (s, 3H); 2.70 (t, 2H, J=7); 2.85 (d, 2H, J=7); 4.9–5.25 (m, 3H); 5.95 (d, 1H, J=17); 6.62 (d×t, 1H, J$_1$=17, J$_2$=7).

The degree of conversion is 80% and the yield based on the converted alcohol is 57%.

6,10,14-Trimethyl-3,6,9,13-pentadecatetraen-2-one may be obtained by proceeding as in Example 38 but changing the nature of the catalyst and, if appropriate, the co-catalyst, the solvent, the temperature and the

EXAMPLE 42

A mixture of 4-isopropenyl-3,7,11-trimethyl-6,10-dodecadien-1-yn-3-ol (0.510 g; 1.96×10$^{-3}$ mole), cuprous chloride (0.0118 g; 1.19×10$^{-4}$ mole) and potassium chloride (0.0142 g; 1.9×10$^{-4}$ mole) is kept stirred for 1 hour at a temperature of 100° C. After the reaction mixture has been filtered through a column of silica and eluted with ethyl ether, followed by evaporation of the eluant, a yellowish oily liquid is obtained, containing, according to vapour phase chromatography, 6% of the starting alcohol and 81.6% of 6,10,14-trimethyl-3,6,9,13-pentadecatetraen-2-one and the isomeric 6,10,14-trimethyl-3,5,9,13-pentadecatetraen-2-one.

Hydrogenation of this mixture under the conditions described in Example 37 produces only 6,10,14-trimethylpentadecan-2-one (phytone) which is in the form of an equimolecular mixture of the two possible diastereoisomers, according to the $^{13}$C NMR spectrum.

EXAMPLE 43

3-Isobutenyl-1-octyn-3-ol (0.180 g; 10$^{-3}$ mole) is kept at a temperature in the region of 40° C. and protected from light, in the presence of silver trifluoromethanesulphonate (0.257 g; 10$^{-3}$ mole) in a mixture (10 cc) of tetrahydrofuran and water (3:1 by volume). After reacting for 7 hours the reaction mixture is treated under the conditions described in Example 1. 2-Methyl-1,4-undecadien-6-one (0.132 g) is obtained, having the following characteristics:

Infrared spectrum (liquid film): characteristic bands at 3,080, 3,040, 1,680, 1,635, 985 and 890 cm$^{-1}$.

NMR spectrum (CDCl$_3$; δ in ppm, J in Hz): 0.83 (t, 3H, J=8); 1.24 (M, 4H); 1.55 (m, 2H); 1.67 (s, 3H); 2.47 (t, 2H, J=11); 2.83 (d, 2H, J=10); 4.68 (broad s, 1H); 4.77 (broad s, 1H), 6.08 (d, 1H, J=22); 6.75 (d×t, 1H, J$_1$=22, J$_2$=10).

The degree of conversion is 100% and the yield based on the converted product is 73%.

EXAMPLE 44

3-Isobutenyl-1-octyn-3-ol (0.180 g; 10$^{-3}$ mole) is kept at the reflux temperature of tetrahydrofuran and protected from light, in the presence of silver nitrate (0.017 g; 10$^{-4}$ mole) and potassium nitrate (0.101 g; 10$^{-3}$ mole) in a mixture (6 cc) of tetrahydrofuran and water (2:1 by volume). After 6 hours of reaction silver nitrate (0.017 g) is again added. Refluxing is continued for another 8.5 hours and the reaction mixture is then treated under the conditions described in Example 1. 2-Methyl-1,4-undecadien-6-one (0.104 g) is obtained.

The degree of conversion is 90% and the yield based on the converted product is 64%.

EXAMPLE 45

5-Methyl-5-hexen-1-yn-3-ol is kept at the reflux temperature of tetrahydrofuran and protected from light, in the presence of silver trifluoromethanesulphonate (0.257 g; $10^{-3}$ mole) in a mixture (10 cc) of tetrahydrofuran and water (3:1 by volume). After reacting for 1 hour the reaction mixture is treated under the conditions described in Example 1. 5-Methyl-2,5-hexadienal (0.060 g) is obtained, having the following characteristics:

Infrared spectrum (liquid film): characteristic bands at 3,070, 3,020, 2,810, 2,730, 1,690, 1,650, 1,125, 970 and 895 cm$^{-1}$.

NMR spectrum (CDCl$_3$; $\delta$ in ppm, J in Hz): 1.78 (s, 3H); 3.02 (d, 2H, J=7); 4.75–4.95 (mt, 2H); 6.15 (d×pert. d, 1H, $J_1$=15, $J_2$=8); 6.87 (d×t, 1H, $J_1$=15, $J_2$=7); 9.56 (d, 1H, J=8).

The degree of conversion is 100% and the yield based on the converted product is 55%.

EXAMPLE 46

5-Methyl-5-hexen-1-yn-3-ol (0.110 g; $10^{-3}$ mole) is kept at the reflux temperature of tetrahydrofuran and protected from light, in the presence of silver nitrate (0.017 g; $10^{-4}$ mole) and potassium nitrate (0.101 g; $10^{-3}$ mole) in a mixture (6 cc) of tetrahydrofuran and water (2:1 by volume). After 5 hours of reaction silver nitrate (0.017 g; $10^{-4}$ mole) is again added, and heating is continued for 1 hour. The reaction mixture is treated under the conditions described in Example 1. 5-Methyl-2,5-hexadienal (0.055 g) is obtained in this way.

The degree of conversion is 100% and the yield based on the converted product is 50%.

EXAMPLE 47

4,8-Dimethyl-5-isopropenyl-7-nonen-2-yn-4-ol is kept at the reflux temperature of tetrahydrofuran and protected from light, in the presence of an equimolecular quantity of silver trifluoromethanesulphonate in a mixture of tetrahydrofuran and water (3:1 by volume). After 21.5 hours of reaction, the reaction mixture is treated under the conditions described in Example 1. 4,6,10-Trimethyl-3,6,9-undecatrien-2-one is thus obtained in a yield of 30%.

EXAMPLE 48

2-Isopropenyl-1-yne cyclododecanol (0.025 g; $10^{-4}$ mole) is kept at a temperature in the region of 60° C. and protected from light, in the presence of silver trifluoromethanesulphonate (0.030 g) in a mixture (1.2 cc) of tetrahydrofuran and water (5:1 by volume). After reacting for 24 hours, the reaction mixture is treated under the conditions described in Example 1. 5-Methyl-2,5-cyclohexadecadiene (0.010 g) is thus obtained, having the following characteristics:

m/e=248

Infrared spectrum (liquid film): characteristic bands at 1,695, 1,670 and 1,623 cm$^{-1}$.

Proton NMR spectrum at 360 MHz (CDCl$_3$; $\delta$ in ppm; J in Hz; hexamethyldisilane internal reference): 1.22 (m, 14H), 1.55 (m, 2H), 1.66 (s, 3H), 1.92 (m, 2H); 2,41 (t, 2H); 2.87 (dd, $J_1$ in the region of 6.5, $J_2$ in the region of 2, 2H); 5.23 (t, J in the region of 7, 1H); 6.04 (dt, $J_1$ in the region of 15, $J_2$ in the region of 1.5, 1H); 6.72 (dt, $J_1$ in the region of 15, $J_2$ in the region of 6.5, 1H).

EXAMPLE 49

4-Isopropenyl-3,7-dimethyl-6-octen-1-yn-3-ol (0.960 g; $5.10^{-3}$ mole) is kept at a temperature in the region of 40° C. and protected from light, in the presence of silver trifluoromethanesulphonate (1.285 g; $5.10^{-3}$ mole) in a mixture (50 cc) of tetrahydrofuran and water (3:1 by volume). After the reaction mixture has reacted for 20 hours and has been treated under the conditions of Example 1, the raw product obtained is hydrogenated in the presence of palladium on charcoal (5% in hexane). After chromatography on a silica column under reduced pressure with elution with a mixture of ether and petroleum-ether (3:7 by volume), 6,10-dimethylundecan-2-one (0.792 g) is obtained, having the following characteristics:

Infrared spectrum (liquid film); characteristic bands at 2,950, 2,920, 2,860, 1,715, 1,460, 1,360, 1,160.

NMR spectrum (CDCl$_3$, $\delta$ in ppm, J in Hz); 0.88 (d, J=6.5, 9H), 1.1–1.8 (M, 12H); 2.12 (s, 3H); 2.4 (t, J=7, 2H).

Mass 198 (M$^+$) (25%), 170 (12%), 137 (12%), 110 (12%), 100 (100%), 85 (95%).

The yield is 80% based on the acetylenic alcohol employed.

We claim:

1. A process for the preparation of an $\alpha,\delta$-diethylenic carbonyl compound of the formula:

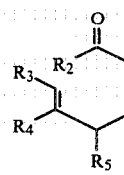

in which R$_1$, R$_2$, R$_3$ and R$_4$, which may be identical or different, each denote a hydrogen atom or a hydrocarbon radical, it being understood that R$_2$ and R$_3$ may together form an alkylene radical (—CH$_2$—)$_n$ in which each of the carbon atoms may be unsubstituted or substituted by one or more alkyl radicals of 1 to 4 carbon atoms each and in which n is an integer from 3 to 20, R$_5$ is hydrogen, and R$_2$ and R$_5$ may together form a ring containing from 6 to 16 chain members, which comprises contacting an acetylenic alcohol of the formula:

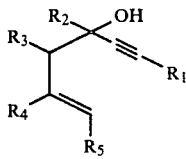

in which R$_1$, R$_2$, R$_3$, R$_4$ and R$_5$ are as defined above, at a temperature below 100° C., with a catalyst chosen from the metals of Group Ib of the periodic table.

2. A process according to claim 1, in which the catalyst is a derivative of copper, silver, or gold.

3. A process according to claim 1, in which the catalyst is cuprous chloride, cuprous bromide, cupric chloride, cuprous acetate, silver trifluoromethanesulphonate, silver nitrate, silver borofluoride, silver acetate, or gold chloride.

4. A process according to claim 1, in which the catalyst is employed in a concentration of 0.001 to 1 mole per mole of acetylenic alcohol employed.

5. A process according to claim 1 which is carried out in the presence of a salt of an alkali metal or a quaternary ammonium salt.

6. A process according to claim 5, in which the salt is a sodium, potassium, lithium or caesium halide, nitrate or trifluoroacetate, or tetrabutyl-ammonium chloride.

7. A process according to claim 1, which is carried out in an organic solvent which is a ketone, alcohol, ether, nitrile, amide, chlorinated solvent, aliphatic hydrocarbon or a mixture thereof, or an aqueous organic mixture.

8. A process according to claim 1, in which in the acetylenic alcohol $R_1$, $R_2$, $R_3$ and $R_4$, which may be identical or different, each denote a hydrogen atom or an acyclic radical of 1 to 20 carbon atoms the chain of which may contain one or more double or triple bonds, $R_2$ and $R_3$ together may denote an alkylene radical $(-CH_2-)_n$ in which each carbon atom is unsubstituted or substituted by one or more alkyl radicals of 1 to 4 carbon atoms each, n is 3 to 20, and $R_5$ is hydrogen.

9. A process according to claim 1, in which in the acetylenic alcohol $R_1$ and $R_5$ each denote a hydrogen atom, $R_2$ and $R_4$ each denote a methyl radical and $R_3$ denotes a 3-methyl-2-butenyl radical or a 3,7-dimethyl-2,6-octadienyl radical.

* * * * *